United States Patent
Nieuwoudt et al.

(10) Patent No.: US 6,383,343 B1
(45) Date of Patent: *May 7, 2002

(54) SEPARATION OF COMPONENTS FROM METHANOL MIXTURES BY EXTRACTIVE DISTILLATION

(76) Inventors: Izak Nieuwoudt, 12 Boschendal Avenue, Karindal, Stellenbosch 7600; Braam van Dyk, 2 Tertius Street, Amandaglen, Durbanville 7550, both of (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 09/671,334

(22) Filed: Sep. 28, 2000

Related U.S. Application Data

(63) Continuation of application No. PCT/IB00/00073, filed on Jan. 26, 2000, and a continuation of application No. PCT/IB00/00077, filed on Jan. 26, 2000.

(30) Foreign Application Priority Data

| Jan. 28, 1999 | (ZA) | 99/0635 |
| Jan. 28, 1999 | (ZA) | 99/0636 |
| Jan. 28, 1999 | (ZA) | 99/0637 |
| Jan. 28, 1999 | (ZA) | 99/0638 |
| Jan. 28, 1999 | (ZA) | 99/0640 |
| Jan. 28, 1999 | (ZA) | 99/0646 |
| Jan. 28, 1999 | (ZA) | 99/0647 |
| Jan. 28, 1999 | (ZA) | 99/0648 |
| Jan. 28, 1999 | (ZA) | 99/0649 |
| Jan. 28, 1999 | (ZA) | 99/0651 |
| Jan. 28, 1999 | (ZA) | 99/0652 |

(51) Int. Cl.[7] .......................... B01D 3/40; C07C 27/32; C07C 29/84; C07C 67/54
(52) U.S. Cl. .......................... 203/57; 203/59; 203/67; 203/68; 203/70; 560/248; 568/410; 568/913
(58) Field of Search .......................... 203/68, 70, 59, 203/63–65, 67, 57; 568/410, 913, 411; 560/248, 265

(56) References Cited

U.S. PATENT DOCUMENTS

| 2,636,050 A | | 4/1953 | Hoaglin et al. |
| 3,960,672 A | * | 6/1976 | Ester et al. .................... 203/37 |
| 4,379,028 A | | 4/1983 | Berg et al. |
| 4,431,838 A | | 2/1984 | Feldman et al. |
| 4,473,444 A | * | 9/1984 | Feldman et al. .............. 203/69 |
| 4,514,262 A | | 4/1985 | Berg |

(List continued on next page.)

FOREIGN PATENT DOCUMENTS

| EP | 0 047 204 A2 | 3/1982 |
| EP | 0 496 060 A2 | 7/1992 |
| GB | 877 360 | 9/1961 |
| JP | 54 119 411 | 9/1979 |

OTHER PUBLICATIONS

Cepeda E et al: "Separacion por destilacion extractiva de mezclas formadas por alcoholes y sus esteres del acido acetico", An. Quim., Ser. A (AQSTDQ, 02111330); 1984; vol. 80 (3, Suppl. 2); pp. 755–759, XP000908880; Col. Univ. Alava; Dep. Quim. Tecn.; Vitoria; Spain (ES) (See English summary on p. 755).

*Primary Examiner*—Virginia Manoharan
(74) *Attorney, Agent, or Firm*—Larson & Taylor PLC

(57) ABSTRACT

A method of separating methanol and acetone, and methanol and methyl acetate involves distilling a mixture of the components by an extractive distillation process in the presence of an extractive distillation solvent. The extractive distillation solvent may be an amine, a chlorinated hydrocarbon, a brominated hydrocarbon, a paraffin, and an alkylated thiopene.

10 Claims, 1 Drawing Sheet

U.S. PATENT DOCUMENTS

| | | | | |
|---|---|---|---|---|
| 4,549,938 A | * | 10/1985 | Berg et al. | 203/57 |
| 4,559,109 A | | 12/1985 | Lee et al. | |
| 4,584,063 A | | 4/1986 | Berg et al. | |
| 4,620,901 A | | 11/1986 | Berg et al. | |
| 4,690,734 A | * | 9/1987 | Berg et al. | 203/60 |
| 4,695,350 A | * | 9/1987 | Berg | 203/64 |
| 4,718,988 A | * | 1/1988 | Berg et al. | 203/60 |
| 4,826,576 A | * | 5/1989 | Berg et al. | 568/913 |
| 5,145,562 A | | 9/1992 | Brown et al. | |
| 5,453,166 A | | 9/1995 | Berg | |
| 5,800,681 A | | 9/1998 | Berg | |
| 5,897,750 A | | 4/1999 | Berg | |

* cited by examiner

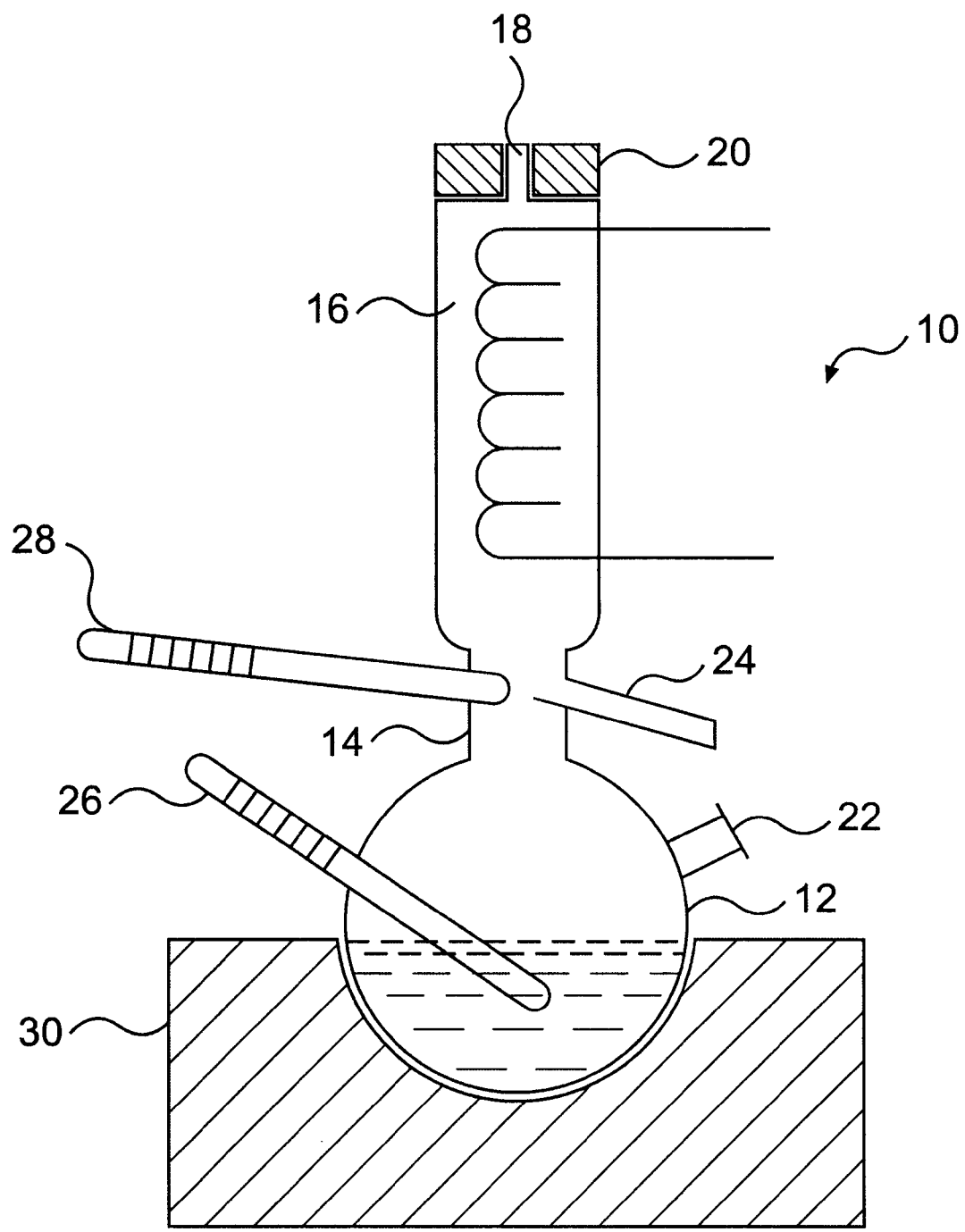

SEPARATION OF COMPONENTS FROM METHANOL MIXTURES BY EXTRACTIVE DISTILLATION

This is a continuation of International PCT Application Numbers PCT/IB00/00073 and PCT/IB00/00077, filed on Jan. 26, 2000.

FIELD OF INVENTION

The present invention relates to the separation of components from methanol mixtures thereof by extractive distillation.

BACKGROUND TO INVENTION

Extractive distillation is a process to separate close-boiling compounds from each other by introducing a selectively-acting third component, the extractive distillation solvent, with the result that the relative volatility of the mixture to be separated is increased and azeotropes, if present, are overcome. The extractive distillation solvent is to be selected such that it does not form an undesired azeotrope with any of the compounds in the mixture.

The separation of methanol and acetone is complicated due to the existence of an azeotrope. Water or ethylene glycol have been proposed in the literature as extractive distillation solvents to produce methanol as distillate.

The separation of methanol and methyl acetate is complicated due to the existence of an azeotrope. 2-Methoxy ethanol has been proposed in the literature as extractive distillation solvents to produce methyl acetate as distillate.

As has been stated in U.S. Pat. No. 5,800,681 (Berg) extractive distillation is the method of separating close boiling compounds from each other by carrying out the distillation in a multiplate rectification column in the presence of an added liquid or liquid mixture, said liquid(s) having a boiling point higher than the compounds being separated. The extractive distillation solvent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive distillation solvent should boil higher than any of the close boiling liquids being separated and not form minimum azeotropes with them. Usually the extractive distillation solvent is introduced a few plates from the top of the column to ensure that none of the extractive distillation solvent is carried over with the lowest boiling component.

It is an object of this invention to suggest at least one further extractive distillation solvent for the separation of components from mixtures thereof.

SUMMARY OF INVENTION

According to the invention, a method of separation of methanol from a mixture of methanol and another compound selected from a first group consisting of acetone and methyl acetate, includes the step of distilling the mixture containing at least methanol and another compound selected from a first group consisting of acetone and methyl acetate by way of an extractive distillaton process in the presence of an extractive distillation solvent selected from a second group consisting of a secondary amine, a chlorinated hydrocarbon, a brominated hydrocarbon, a paraffin, an amine, a halogenated hydrocarbon, an alkylated thiopene and a diol.

The mixture may contain methanol and acetone and the extractive distillation solvent may be selected from a group consisting of a secondary amine, a chlorinated hydrocarbon, a brominated hydrocarbon and a paraffin.

The methanol and acetone mixture may contain only methanol and acetone.

The secondary amine may be selected from a group consisting of N,N'-dimethyl-1,3-propanediamine, N,N'-dimethylethylenediamine and dibutylamine.

The chlorinated hydrocarbon may be selected from a group consisting of hexachlorobutadiene and tetrachloroethylene.

The brominated hydrocarbon may be 1,4-dibromobutane.

The paraffin may be at least one of the components selected from a group consisting of undecane, dodecane, tridecane and tetradecane.

The mixture may contain methanol and methyl acetate and the extractive distillation solvent may be selected from a group consisting of an amine, a halogenated hydrocarbon, an alkylated thiopene, a diol and a paraffin.

The methanol and methyl acetate mixture may contain only methanol and methyl acetate.

The amine may be selected from a group consisting of N,N'-dimethylethylenediamine, N,N'-dimethyl-1,3-propanediamine, diethylenetriamine, hexamethylenediamine, 1,4-diaminobutane and 1,3-diaminopentane.

The halogenated hydrocarbon may be selected from a group consisting of hexachlorobutadiene, tetrachloroethylene and dibromobutane.

The alkylated thiopene may be ethyl thiopene.

The diol may be diethylene glycol.

The paraffin may be at least one of the components selected from a group consisting of undecane, dodecane, tridecane and tetradecane.

BRIEF DESCRIPTION OF DRAWING

The invention will now be described by way of example with reference to the accompanying schematic drawing.

In the drawing there is shown a schematic view of an experimental apparatus for testing an extractive distillation solvent for separating components from mixtures thereof in accordance with the invention.

DETAIL DESCRIPTION OF THE PREFERRED EMBODIMENTS

In the drawing there is shown a vapour-liquid equilibrium still 10 including a bulb flask 12 having a tube 14 leading to a condenser 16 and terminating in an outlet 18. The outlet 18 has an electromagnetic closure mechanism 20.

A liquid phase sample conduit 22 leads into the flask 12.

A further liquid phase sample conduit 24 leads into the tube 14.

A first thermometer 26 is adapted to read the temperature of the liquid contained in the flask 12, and a second thermometer 28 is adapted to read the temperature of the vapour in the tube 14.

The flask 12 can be heated by a heating mantle 30.

The extractive distillation procedure is as follows:

A liquid mixture is prepared consisting of the components to be separated and an extractive distillation solvent. The liquid is introduced into the bulb flask 12 via conduit 22.

The mixture in the bulb flask 12 is then heated by the heating mantle 30 and kept at boiling point.

During boiling the mixture separates into a liquid phase remaining in the bulb flask 12 and a vapour phase in the tube 14. In the tube 14 the vapour phase is cooled by the condenser 16, whereafter it condenses and returns as liquid to the bulb flask 12.

The mixture is boiled and condensed for several hours, normally 5 to 6 hours. The process of evaporation and condensation is repeated until equilibrium is reached between the vapour and liquid phases. Thereafter, a liquid sample of the liquid phase in the bulb flask 12 is extracted through conduit 22 and a liquid sample of the condensed vapour phase in the tube 14 is extracted through conduit 24.

The temperature of the liquid phase in the bulb flask 12 is continuously monitored by the thermometer 26, and the temperature of the vapour phase in the tube 14 is continuously monitored by the thermometer 28.

EXPERIMENT 1

A methanol/acetone liquid mixture with a molar ratio of 1.55:1 has a relative volatility of 0.63.

The separation was effected by using a suitable secondary amine as an extractive distillation solvent.

A mixture of methanol (8.1 g), acetone (9.4 g) and N,N'-dimethylethylene diamine (39.5 g) was charged into the flask 12 of the vapour-liquid equilibrium still 10 and the above procedure was applied. The liquid and vapour phases were analysed. The liquid and vapour molar fractions were determined to be as follows:

TABLE 1

| Component | Liquid (mole fraction) | Vapour (mole fraction) |
| --- | --- | --- |
| Methanol | 0.293 | 0.914 |
| Acetone | 0.188 | 0.076 |
| N,N'-dimethylethylenediamine | 0.519 | 0.010 |

This translates to a relative volatility of 7.73 for the system methanol/acetone in the ternary system shown above, the methanol being the distillate.

EXPERIMENT 2

An acetone/methanol mixture with a molar ratio of 1:1 has a relative volatility of 1.4.

The separation was effected by a suitable secondary amine as an extractive distillation solvent.

A mixture of methanol (7.9 g), acetone (14.4 g) and di-butylamine (245.3 g) was charged into the flask 12 of the vapour-liquid equilibrium still 10 and the above procedure was applied. The liquid and vapour phases were analysed. The liquid and vapour molar fractions were is determined to be as follows:

TABLE 2

| Component | Liquid (mole fraction) | Vapour (mole fraction) |
| --- | --- | --- |
| Methanol | 0.103 | 0.337 |
| Acetone | 0.104 | 0.636 |
| Di-butylamine | 0.793 | 0.027 |

This translates to a relative volatility of 1.88 for the system acetone/methanol in the ternary system shown above, the acetone being the distillate.

EXPERIMENT 3

A methanol/acetone mixture with a molar ratio of 0.85:1 has a relative volatility of 0.75.

The separation was effected by using a suitable chlorinated hydrocarbon as an extractive distillation solvent.

A mixture of methanol (11.7 g), acetone (24.9 g) and tetrachloroethylene (491.0 g) was charged into the flask 12 of the vapour-liquid equilibrium 10 and the above procedures was applied. The liquid and vapour phases were analysed. The liquid and vapour molar fractions were determined to be as follows:

TABLE 3

| Component | Liquid (mole fraction) | Vapour (mole fraction) |
| --- | --- | --- |
| Methanol | 0.097 | 0.558 |
| Acetone | 0.114 | 0.351 |
| Tetrachloroethylene | 0.788 | 0.091 |

This translates to a relative volatility of 1.87 for the system methanol/acetone in the ternary system shown above, the methanol being the distillate.

EXPERIMENT 4

A methanol/acetone mixture with a molar ratio of 0.63:1 has a relative volatility of 0.81.

The separation was effected by using a suitable chlorinated hydrocarbon as an extractive distillation solvent.

After sampling in experiment 3, the mixture left in the apparatus was boiled up again (for 5 to 6 hours) and liquid and vapour samples drawn. The liquid and vapour phases were analysed. The liquid and vapour molar fractions were determined to be as follows:

TABLE 4

| Component | Liquid (mole fraction) | Vapour (mole fraction) |
| --- | --- | --- |
| Methanol | 0.062 | 0.556 |
| Acetone | 0.099 | 0.347 |
| Tetrachloroethylene | 0.839 | 0.097 |

This translates to a relative volatility of 2.57 for the system methanol/acetone in the ternary system shown above, the methanol being the distillate.

EXPERIMENT 5

A methanol/acetone mixture with a molar ratio of 1.1:1 has a relative volatility of 0.70.

The separation was effected by using a suitable brominated hydrocarbon as an extractive distillation solvent.

A mixture of methanol (11.6 g), acetone (6.9 g) and 1,4-dibromobutane (173.1 g) was charged into the flask 12 of the vapour-liquid equilibrium still 10 and the above procedure was applied. The liquid and vapour phases were analysed. The liquid and vapour molar fractions were determined to be as follows:

TABLE 5

| Component | Liquid (mole fraction) | Vapour (mole fraction) |
| --- | --- | --- |
| Methanol | 0.177 | 0.868 |
| Acetone | 0.164 | 0.131 |
| 1,4-dibromobutane | 0.659 | 0.001 |

This translates to a relative volatility of 6.12 for the system methanol/acetone in the ternary system shown above, the methanol being the distillate.

EXPERIMENT 6

A methanol/acetone mixture with a molar ratio of 1.13:1 has a relative volatility of 0.69.

The separation was effected by using a suitable paraffin as an extractive distillation solvent.

A mixture of methanol (6.3 g), acetone (10.2 g) and dodecane (207.3 g) was charged into the flask 12 of the vapour-liquid equilibrium still 10 and the above procedure was applied. The liquid and vapour phases were analysed. The liquid and vapour molar fractions were determined to be as follows:

TABLE 6

| Component | Liquid (mole fraction) | Vapour (mole fraction) |
| --- | --- | --- |
| Methanol | 0.124 | 0.634 |
| Acetone | 0.110 | 0.363 |
| Dodecane | 0.766 | 0.004 |

This translates to a relative volatility of 1.56 for the system methanol/acetone in the ternary system shown above, the methanol being the distillate.

EXPERIMENT 7

A methanol/methyl acetate liquid mixture with a molar ratio of 1:1 has a relative volatility of 0.73.

The separation was effected by using a suitable amine as an extractive distillation solvent.

A mixture of methanol (7.6 g), methyl acetate (19.1 g) and 1,3-diaminopentane (190.6 g) was charged into the flask 12 of the vapour-liquid equilibrium still 10 and the above procedure was applied. The liquid and vapour phases were analysed. The liquid and vapour molar fractions were determined to be as follows:

TABLE 7

| Component | Liquid (mole fraction) | Vapour (mole fraction) |
| --- | --- | --- |
| Methanol | 0.101 | 0.746 |
| Methyl Acetate | 0.109 | 0.235 |
| 1,3-diaminopentane | 0.790 | 0.018 |

This translates to a relative volatility of 3.44 for the system methanol/methyl acetate in the ternary system shown above, the methanol being the distillate.

EXPERIMENT 8

A methanol/methyl acetate mixture with a molar ratio of 0:97 has a relative volatility of 1.40.

The separation was effected by using a suitable amine as an extractive distillation solvent.

A mixture of methanol (8.3 g), methyl acetate (18.6 g) and 1,4-diaminobutane (88.6 g) was charged into the flask 12 of the vapour-liquid equilibrium still 10 and the above procedures was applied. The liquid and vapour phases were analysed. The liquid and vapour molar fractions were determined to be as follows:

TABLE 8

| Component | Liquid (mole fraction) | Vapour (mole fraction) |
| --- | --- | --- |
| Methanol | 0.171 | 0.354 |
| Methyl Acetate | 0.166 | 0.646 |
| 1,4-Diaminobutane | 0.663 | 0.001 |

This translates to a relative volatility of 1.88 for the system methyl acetate/methanol in the ternary system shown above, the methyl acetate being the distillate.

EXPERIMENT 9

A methanol/methyl acetate mixture with a molar ratio of 1:1 has a relative volatility of 0.72.

The separation was effected by using a suitable chlorinated hydrocarbon as an extractive distillation solvent.

A mixture of methanol (13.5 g), methyl acetate (30.9 g) and tetrachloroethylene (483.4 g) was charged into the flask 12 of the vapour-liquid equilibrium still 10 and the above procedure was applied. The liquid and vapour phases were analysed. The liquid and vapour molar fractions were determined to be as follows:

TABLE 9

| Component | Liquid (mole fraction) | Vapour (mole fraction) |
| --- | --- | --- |
| Methanol | 0.112 | 0.652 |
| Methyl Acetate | 0.111 | 0.262 |
| Tetrachloroethylene | 0.776 | 0.086 |

This translates to a relative volatility of 2.46 for the system methanol/methyl acetate in the ternary system shown above, the methanol being the distillate.

EXPERIMENT 10

A methanol/methyl acetate mixture with a molar ratio of 0:54:1 has a relative volatility of 0.98.

The separation was effected by using a suitable chlorinated hydrocarbon as an extractive distillation solvent.

After sampling in experiment 3, the mixture left in the apparatus was boiled up again (5 to 6 hours) and the vapour and liquid phases sampled. The liquid and vapour phases were analysed. The liquid and vapour molar fractions were determined to be as follows:

TABLE 10

| Component | Liquid (mole fraction) | Vapour (mole fraction) |
| --- | --- | --- |
| Methanol | 0.051 | 0.592 |
| Methyl Acetate | 0.094 | 0.331 |
| Tetrachloroethylene | 0.855 | 0.077 |

This translates to a relative volatility of 3.30 for the system methanol/methyl acetate in the ternary system shown above, the methanol being the distillate.

EXPERIMENT 11

A methanol/methyl acetate mixture with a molar ratio of 0.46:1 has a relative volatility of 1.05.

The separation was effected by using a suitable alkylated thiophene as an extractive distillation solvent.

A mixture of methanol (6.2 g), methyl acetate (10.6 g) and ethylthiophene (44.0 g) was charged into the flask 12 of the vapour-liquid equilibrium still 10 and the above procedure was applied. The liquid and vapour phases were analysed. The liquid and vapour molar fractions were determined to be as follows:

TABLE 11

| Component | Liquid (mole fraction) | Vapour (mole fraction) |
| --- | --- | --- |
| Methanol | 0.130 | 0.484 |
| Methyl Acetate | 0.281 | 0.504 |
| Ethylthiophene | 0.589 | 0.011 |

This translates to a relative volatility of 2.07 for the system methanol/methyl acetate in the ternary system shown above, the methanol being the distillate.

EXPERIMENT 12

A methanol/methyl acetate mixture with a molar ratio of 1:1 has a relative volatility of 0.72.

The separation was effected by using a suitable diol as an extractive distillation solvent.

A mixture of methanol (13.0 g), methyl acetate (29.9 g) and ethylene glycol (200.7 g) was charged into the flask 12 of the vapour-liquid equilibrium still 10 and the above procedure was applied. The liquid and vapour phases were analysed. The liquid and vapour molar fractions were determined to be as follows:

TABLE 12

| Component | Liquid (mole fraction) | Vapour (mole fraction) |
| --- | --- | --- |
| Methanol | 0.100 | 0.221 |
| Methyl Acetate | 0.100 | 0.721 |
| Ethylene Glycol | 0.800 | 0.059 |

This translates to a relative volatility of 3.28 for the system methanol/methyl acetate in the ternary system shown above, the methyl acetate being the distillate.

EXPERIMENT 13

A methanol/methyl acetate mixture with a molar ratio of 3.3:1 has a relative volatility of 0.43.

The separation was effected by using a suitable paraffin as an extractive distillation solvent.

A mixture of methanol (23.1 g), methyl acetate (16.8 g) and dodecane (234.5 g) was charged into the flask 12 of the vapour-liquid equilibrium still 10 and the above procedure was applied. The liquid and vapour phases were analysed. The liquid and vapour molar fractions were determined to be as follows:

TABLE 13

| Component | Liquid (mole fraction) | Vapour (mole fraction) |
| --- | --- | --- |
| Methanol | 0.312 | 0.837 |
| Methyl Acetate | 0.093 | 0.162 |
| Dodecane | 0.596 | 0.001 |

This translates to a relative volatility of 1.54 for the system methanol/methyl acetate in the ternary system shown above, the methanol being the distillate.

EXPERIMENT 14

A methanol/methyl acetate mixture with a molar ratio of 1:1.03 has a relative volatility of 0.73.

The separation was effected by using a suitable amine as an extractive distillation solvent.

A mixture of methanol (6.5 g), methyl acetate (15.4 g) and hexamethylenediamine (181.2 g) was charged into the flask 12 of the vapour-liquid equilibrium still 10 and the above procedure was applied. The liquid and vapour phases were analysed. The liquid and vapour molar fractions were determined to be as follows:

TABLE 14

| Component | Liquid (mole fraction) | Vapour (mole fraction) |
| --- | --- | --- |
| Methanol | 0.103 | 0.972 |
| Methyl Acetate | 0.106 | 0.028 |
| Hexamethylenediamine | 0.791 | 0.000 |

This translates to a relative volatility of 35.7 for the system methanol/methyl acetate in the ternary system shown above, the methanol being the distillate.

What is claimed is:

1. A method of separation of methanol and acetone, comprising distilling a mixture of methanol and acetone containing at least methanol and acetone by an extractive distillation process in the presence of an extractive distillation solvent selected from the group consisting of a secondary amine, a chlorinated hydrocarbon, a brominated hydrocarbon, and a paraffin.

2. The method as claimed in claim 1, wherein the methanol and acetone mixture contains only methanol and acetone.

3. The method as claimed in claim 1, wherein the secondary amine is selected from the group consisting of N,N'-dimethyl-1,3-propanediamine, N,N'-dimethylethylenediamine and dibutylamine.

4. The method as claimed in claim 1, wherein the chlorinated hydrocarbon is selected from the group consisting of hexachlorobutadiene and tetrachloroethylene.

5. The method as claimed in claim 1, wherein the brominated hydrocarbon is 1,4-dibromo-butane.

6. The method as claimed in claim 1, wherein the paraffin is selected from the group consisting of undecane, dodecane, tridecane and tetradecane.

7. A method of separation of methanol and methyl acetate, comprising distilling a mixture of methanol and methyl acetate containing at least methanol and methyl acetate by an extractive distillation process in the presence of an extractive distillation solvent selected from the group consisting of an amine, hexachlorobutadiene, tetrachloroethylene, dibromobutane, an alkylated thiopene, undecane, dodecane, tridecane, and tetradecane.

8. The method as claimed in claim 7, wherein the methanol and methyl acetate mixture contains only methanol and methyl acetate.

9. The method as claimed in claim 7, wherein the amine is selected from the group consisting of N,N'-dimethylethylenediamine, N,N'-dimethyl-1,3-propanediamine, diethylenetriamine, hexamethylenediamine, 1,4-diaminobutane and 1,3-diaminopentane.

10. The method as claimed in claim 7, wherein the alkylated thiopene is ethyl thiopene.

* * * * *